United States Patent [19]

Lewis

[11] Patent Number: 5,056,464
[45] Date of Patent: Oct. 15, 1991

[54] AUTOMATED INJECTION SYSTEM FOR AVIAN EMBRYOS WITH ADVANCED FLUID DELIVERY SYSTEM

[75] Inventor: Robert H. Lewis, Cary, N.C.

[73] Assignee: Embrex, Inc., Durham, N.C.

[21] Appl. No.: 466,878

[22] Filed: Jan. 18, 1990

[51] Int. Cl.⁵ ............................................. A01K 45/00
[52] U.S. Cl. ..................................................... 119/6.8
[58] Field of Search ........................... 119/6.8; 426/2; 198/468.3; 294/65

[56] References Cited

U.S. PATENT DOCUMENTS

| | | | |
|---|---|---|---|
| 2,477,752 | 8/1949 | Kiss | 119/6.8 |
| 2,762,365 | 9/1956 | Wagner et al. | |
| 3,013,833 | 12/1961 | Gwin et al. | 294/65 |
| 3,077,993 | 2/1963 | Mulvany et al. | |
| 3,123,045 | 3/1964 | Cosgrove et al. | 119/6.8 |
| 3,139,300 | 6/1964 | Hirt | 294/65 |
| 3,256,856 | 6/1966 | Nicely | 119/6.8 |
| 3,321,087 | 5/1967 | Fuge et al. | 119/6.8 X |
| 3,377,989 | 4/1968 | Sandhage et al. | 119/6.8 |
| 3,420,743 | 1/1969 | Sandhage et al. | |
| 3,486,982 | 12/1969 | Noren | |
| 3,506,140 | 4/1970 | Koch et al. | |
| 3,594,285 | 7/1971 | Noren | |
| 3,616,262 | 10/1971 | Coady et al. | |
| 3,934,916 | 1/1976 | Baker | 294/65 X |
| 4,019,430 | 4/1977 | Warren | 99/485 |
| 4,040,388 | 8/1977 | Miller | 119/6.8 |
| 4,355,936 | 10/1982 | Thomas et al. | |
| 4,469,047 | 9/1984 | Miller | 119/6.8 |
| 4,593,646 | 6/1986 | Miller et al. | 119/6.8 |
| 4,681,063 | 7/1987 | Hebrank | 119/6.8 |

Primary Examiner—Robert P. Swiatek
Attorney, Agent, or Firm—Bell, Seltzer, Park & Gibson

[57] ABSTRACT

The invention is an apparatus for automatically injecting eggs with a desired fluid such as a medical vaccine. The inventon eliminates the pumping of fluids through conventional fluid handling systems and thereby increases the accuracy and precision of volume delivery while eliminating such of the possiblity of contamination of the fluid and the system. The apparatus comprises a syringe having a delivery tip and a portion for containing a predetermined quantity of fluid, a plunger operatively associated with the syringe for intaking and delivering fluids through the delivery tip, a platform for aligning a fluid reservoir with the delivery tip of the syringe so that fluid from the reservoir may be intaken through the delivery tip and into the fluid containing portion, a punch for forming a small opening in the shell of an egg, and horizontally disposed and vertically moveable plates for moving the delivery tip of the syringe through the opening in an egg formed by the punch so that the plunger can deliver a fluid through the delivery tip, through the opening and into the egg to be treated by the fluid.

29 Claims, 6 Drawing Sheets

AUTOMATED INJECTION SYSTEM FOR AVIAN EMBRYOS WITH ADVANCED FLUID DELIVERY SYSTEM

FIELD OF THE INVENTION

The present invention relates to the automatic injection of eggs with fluid substances and in particular relates to an improved system for handling the fluid substances.

BACKGROUND OF THE INVENTION

Injection of eggs with fluid substances has typically been used to incubate certain vaccines which have medical applications, as eggs provide an appropriate environment for the growth of such vaccine materials. More recently, however, as developments in the field of poultry embryology have become more advanced, it has become desireable to add various substances to the embryo or to the environment around the embryo within an avian egg for the purpose of encouraging beneficial effects in the subsequently hatched chick. Such beneficial effects include increased growth, prevention of disease, increasing the percentage hatch of large numbers of incubated eggs, and otherwise improved physical characteristics of hatched poultry. Additionally, certain types of vaccination which could heretofore only be carried out upon either recently hatched or fully mature poultry, can now be successfully accomplished upon an embryonated egg.

One traditional method of injecting eggs has been injection by hand. Skilled operators can inject eggs by hand with some success, but the speed and accuracy of the process is limited. Additionally, hand injection of eggs, even by skilled operators, does not always result in continuous repeated precision delivery of materials to a desired particular location within an egg. Thus, practical techniques and methodologies for high speed precision application of active substances into eggs is a desirable development.

Additionally, where such injection techniques can replace hand injection of very young chicks (typically dayold chicks), beneficial increases in efficiency can be accomplished, and the stress of injection on chicks which are so young can be significantly reduced.

A number of automatic devices have been disclosed for injecting eggs. These include patents to Sandhage, U.S. Pat. No. 3,377,989 and to Miller, U.S. Pat. Nos. 4,040,388; 4,469,047; and 4,593,645. Additionally, a particularly successful injection device is disclosed in Hebrank U.S. Pat. No. 4,681,063 which is assigned to the assignee of the present invention. A review of all of these patents and their associated systems reveals, however, that all require that fluid be delivered to the egg through an injection needle and in turn that the fluid be delivered to the needle through a rather complicated system of pumps and tubing which carries the fluid from some type of stock storage to the needle.

As would be expected, when an injection device is placed in contact with a large number of eggs--which indeed is the purpose of such a machine--contamination of any one or more of the needles may occur. For example, a needle encountering an egg which has died during incubation can easily become contaminated by the materials in the dead egg. In turn, with the needle so contaminated, especially with biological impurities, it is likely that the tubing, stock supplies and other portions of the delivery system can likewise be contaminated. When this is the case, in order to prevent contamination of large number of eggs which are later handled and injected by the machine, it becomes necessary to halt the entire injection operation, and thoroughly clean, disinfect or otherwise renew the device, all before continuing with the injection the machine was intended for in the first place. As might be expected, the time spent clearing up any such problem drastically reduces the speed and efficiency for which the machine was intended.

As another consideration in egg injection, where specific vaccines or other sensitive materials are to be delivered, the specific quantity delivered is often an important parameter. This is especially true when very small quantities of materials must be delivered. For example, in some treatments of avian embryos, microliter quantities are often desired. The large systems of pumps and tubing used heretofore in injection machines makes accurate and precise delivery of such small quantities rather difficult.

Accordingly, it is an object of the invention to provide an automated injection system for embryos within eggs which has an advanced fluid delivery system which eliminates the pumping of fluids through conventional fluid handling systems and thereby reduces or eliminates the possibility of the contamination of the fluid and provides a more accurate volume delivery of such fluids.

SUMMARY OF THE INVENTION

The present invention addresses this object by providing an apparatus and method which utilizes a syringe which has a needle-type delivery tip and a portion for containing a predetermined quantity of fluid. Means operatively associated with the needle aspirate and deliver fluids through the delivery tip of the needle, while means for aligning a fluid reservoir with the delivery tip of the needle are included so that fluid from the reservoir can be aspirated through the delivery tip and into the fluid containing portion. The invention includes means for forming a small opening in the shell of an egg and means for moving the delivery tip of the needle through the opening in the egg formed by the opening forming means. The needle can thus deliver a fluid through the delivery tip into the egg to be treated by the fluid. The path of fluid into and out of the injection system is limited to the injection needle and its fluid containing portion so that the possibility of widespread contamination is greatly reduced and the accuracy and precision of the fluid volume delivery is greatly increased.

The foregoing and other objects, advantages and features of the invention, and the manner in which the same are accomplished, will become more readily apparent upon consideration of the following detailed description of the invention taken into conjunction with the accompanying drawings, which illustrate preferred and exemplary embodiments, and wherein:

DETAILED DESCRIPTION OF THE PREFERRED EMBODIMENT

Figure 8:
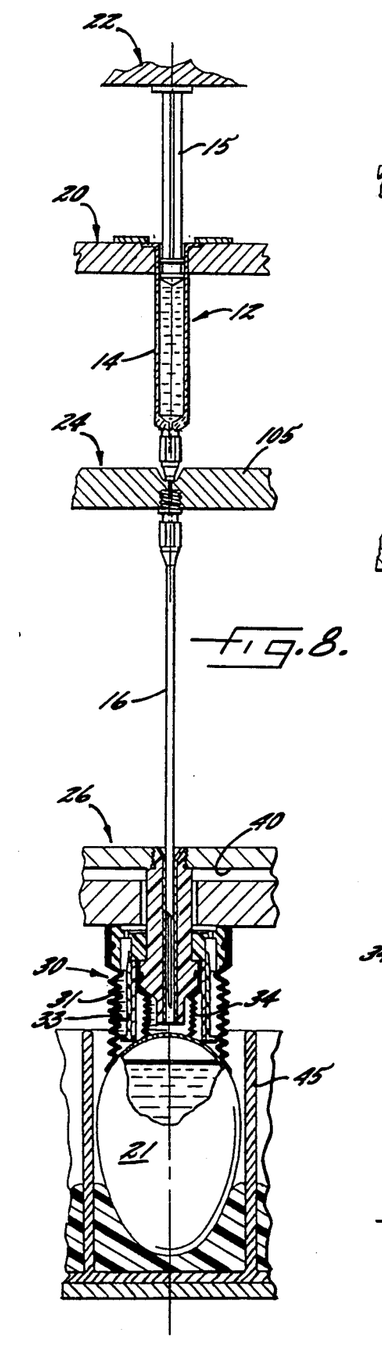
FIGS. 8, 9 and 10 are enlarged cross-sectional views illustrating the injection operation of the present invention.
Figure 9:
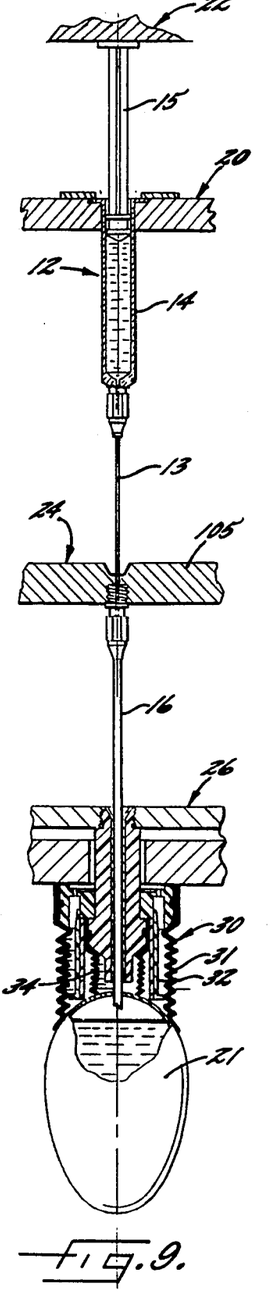
Figure 10:
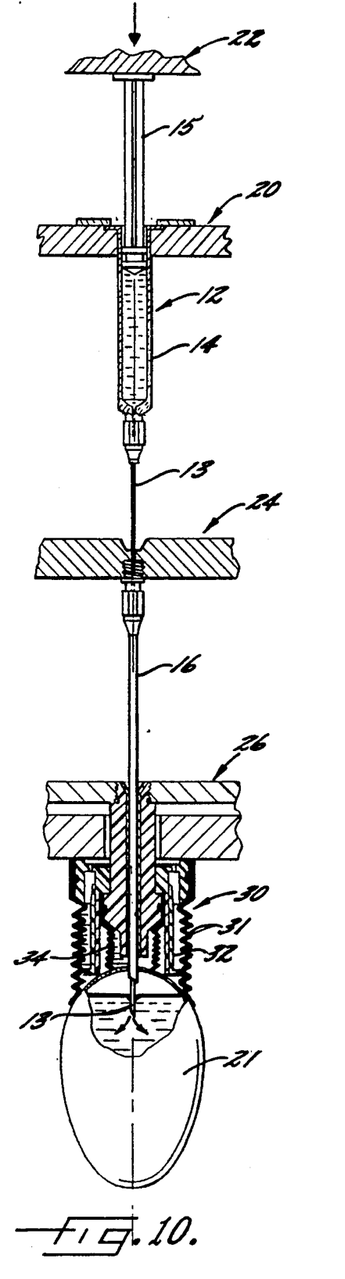

The present invention is an apparatus broadly designated at 10 (FIG. 1) for automatically injecting eggs with a desired fluid such as a medical vaccine. The device eliminates the pumping of fluids through conventional fluid handling systems and thereby increases the accuracy and precision of volume delivery while eliminating much of the possibility of contamination of the fluid and the system. The apparatus comprises a plurality of syringes each broadly designated at 12 (FIGS. 8-10). Each syringe has a delivery tip illustrated as the injection needle 13 and a portion shown as the barrel 14 for containing a predetermined quantity of fluid.

Means shown as the plungers 15 are operatively associated with each syringe 12 for intaking and delivering fluids through the injection needles 13. The apparatus 10 also includes means shown as the punches 16 for forming a small opening in the shell of an egg broadly designated at 21.

Figure 1:
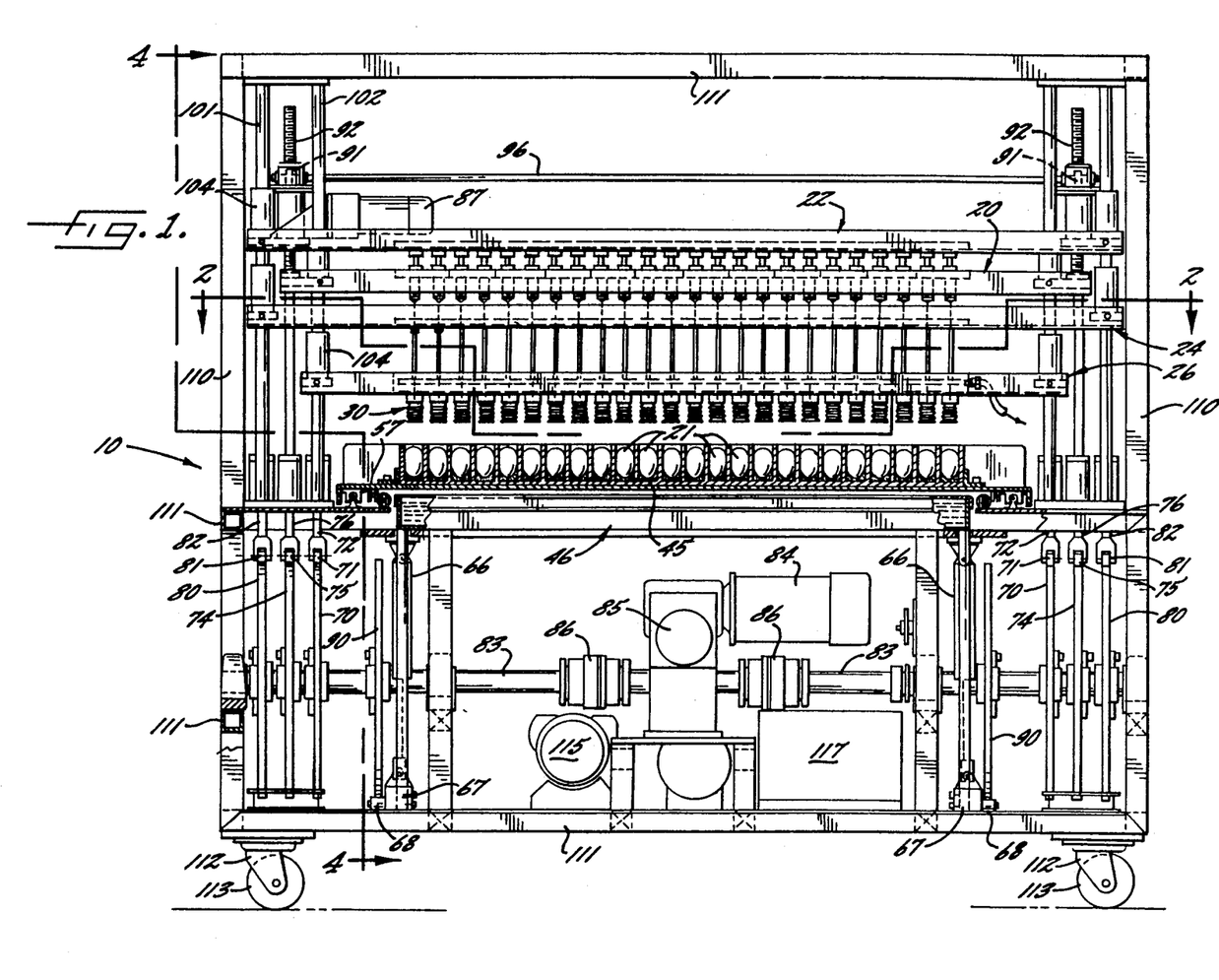
FIG. 1 is a side elevational view of an egg injection system according to the present invention.

The apparatus further includes means for moving the delivery tips 13a of the syringes 12 through an opening in an egg 21 formed by the punches 16 so that the intake and delivery means can deliver a fluid through the delivery tip 13a, through an opening, and into an egg to be treated by the fluid. In the drawings, these means are illustrated as the four plates broadly designated at 21, 22, 24, and 26. FIG. 1 illustrates the overall relationship between these plates and the apparatus 10, while FIGS. 8-13 help clarify their operation. As will be described herein, these plates move in relationship to one another to control the movement of the syringes 12, including their injection needles 13, barrels 14, and plungers 15, as well as the punches 16 and other portions of the apparatus 10.

The first horizontally disposed and vertically movable plate is designated broadly at 20 and carries a plurality of the syringes 12 in a downward vertically disposed direction with the syringes 12 fixed to the plate 20 so that the movement of the syringes 12 follows the vertical movement of the first plate.

The second horizontally disposed and vertically movable plate is broadly designated at 22 and as shown in the drawings is positioned above the first plate 20. In particular, the second plate 22 is operatively associated with the plungers 15 so that the movement of the plungers 15 follows the movement of the second plate 22 to thereby draw fluid into or force fluid out of the barrels 14 through the injection needles 10 as the second plate 22 moves in a vertical fashion.

The third horizontally disposed and vertically movable plate is designated at 24 and is positioned below the first plate and carries a plurality of the punches 16. Each of the punches 16 respectively surrounds one of the injection needles 10 that depend from the first plate 20. The punches 16 function to form a small opening in the shell of an egg 21 so that the vertical movement of the punches 16 follows the vertical movement of the third plate 24.

A fourth horizontally disposed and vertically movable plate is broadly designated at 26 and is positioned below the third plate 24. The fourth plate 26 carries a plurality of flexible suction cups broadly designated at 30. Each of the suction cups 30 respectively surrounds one of the punches 16 which in turn respectively surrounds one of the injection needles 13. In operation, the suction cups 30 are received in seated sealing relation against upwardly facing shell portions of an egg 21.

In somewhat more detail, it will be seen that the suction cups 30 provide the means for aligning each egg in a particular position with respect to the apparatus 10 with the result that the injection needles 13 and the openings in the eggs 20 formed by the punches 16 are in a predetermined position with respect to one another. By way of further detail, it will be seen that each of the tubular punches 16 preferably has a beveled tip for facilitating formation of an opening in an egg 21.

As perhaps best illustrated in FIGS. 7-10, the cups 30 include means for providing suction to each cup, which can be provided through the use of a conventional vacuum pump, so that the suction seats the upwardly facing shell portions of an egg 21 against the cup in a predetermined aligned position with respect to the syringe 12. In order to accomplish this, each of the cups 30 includes a generally cylindrical and collapsible outer bellows 31. When the bellows 31 is placed in contact with the shell of an egg 21 and suction is applied to the interior of the bellows 31, the suction draws the egg 21 into seated sealing relation with the bellows 31 and consequently with the entire cup 30.

Figures 5, 6, 7:
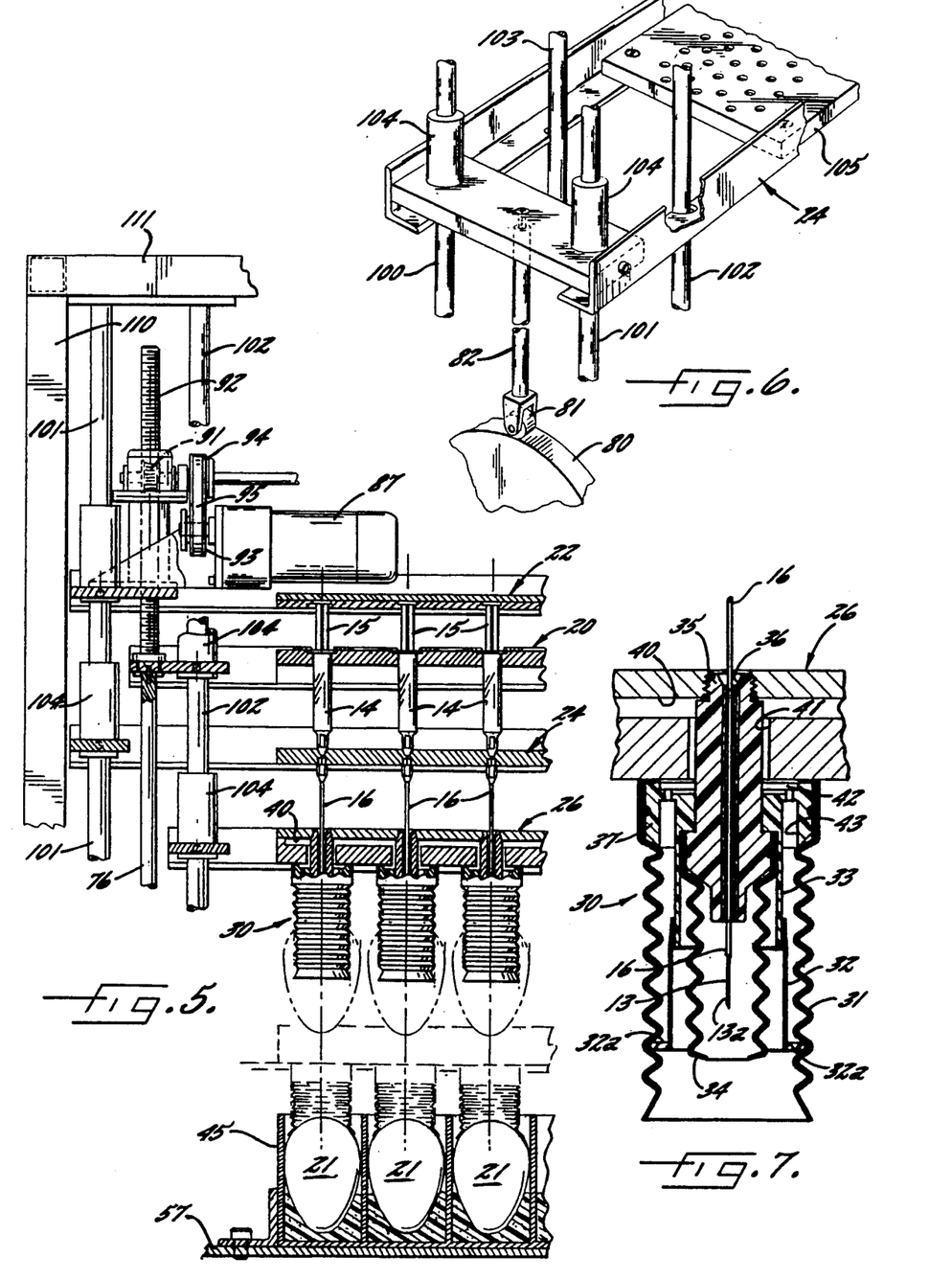
FIG. 5 is an enlarged partial cross-sectional view of a portion of the apparatus illustrated in FIG. 1 and showing some of the features of the device in more detail.
FIG. 6 is a partial sectional view of some elements of the apparatus shown apart from the remainder of the apparatus.
FIG. 7 is a view of the suction devices used in conjunction with the present invention.

As illustrated FIGS. 7-13, in the preferred embodiment each cup 30 includes means, shown as the relatively rigid cylinder 32 carried on shoulders 32a by the outer bellows 31. The cylinder 32 is positioned coaxially with the inner and outer bellows, for controlling the collapse of the cup when suction is applied thereto. The cylinder 32 prevents the bellows 31 from collapsing inwardly when suction is applied and instead encourages the bellows 31 to collapse longitudinally in the desired fashion. As the bellows 31 collapses, it carries Cylinder 32 upwardly in a sliding fashion over corresponding cylinder 33, both of which are made of a relatively low friction material such as an appropriate plastic or polymer (FIG. 7).

As further illustrated in FIG. 7, each cup 30 also includes means shown as the generally cylindrical and collapsible inner bellows 34 positioned coaxially inside the outer bellows 31 for preventing suction from being applied through the punch-formed opening in an egg 21 while the egg is held by suction in seated sealing relation with the suction cup 30. In summary, when an egg 21 is in seated sealing relation with a cup 30, suction is applied in the annular shaped channel formed between the outer bellows 31 and the inner bellows 34 so that the suction which is applied to hold the egg in place is prevented from affecting the interior of the punched egg FIG. 7 also illustrates that in a currently preferred embodiment the cup 30 is mounted on the fourth plate 26 using a threaded fixture 35 also preferably formed of a molded polymeric material, which has a central longitudinally extending opening 36 through which both the punch 16 and the injection needle 13 can extend to reach the egg 21 when the egg is seated against the cup 30. In the illustrated embodiment, the fixture 35 is illustrated as having shoulders upon which another molded fixture 37 can rest so that threading fixture 35 into plate 26 urges and holds fixture 37 against plate 26 and in turn fixture 37 holds the outer bellows 31 in place while fixture 35 holds the inner bellows 34 in place. It will be understood, however, that this particular arrangement is illustrative of one presently preferred manner in which the cup can be maintained adjacent the plate 26 and is not limiting of the invention.

In order to provide suction to the cups 30 and in turn to the eggs 21, plate 26 includes a channel 40 to which a vacuum is applied. Channel 40 is in respective communication with passage 41 in plate 26 and passages 42 and 43 in fixture 37. These in turn open into the annular chamber between bellows 31 and bellows 34 through Which suction is desirably applied to an egg 21.

Although not illustrated, fixture 35 can also include a longitudinal bleed hole or opening extending along its length so that as the cup 30 engages an egg with suction applied and bellows 31 and 34 begin to collapse, the air trapped within bellows 34 may escape more quickly and bellows 34 may collapse correspondingly more smoothly. If such an opening is not provided, the air can escape through the central cylindrical opening 36 which may be sufficient or advantageous in some cases, but in other cases the additional opening is preferred.

FIG. 7 illustrates the cup 30 and the associated assembly in an extended position and not in contact with an egg, while FIGS. 8, 9 and 10, which are on a somewhat smaller scale, illustrate the same structure as FIG. 7 in the egg-engaging collapsed orientation. Because of the multiplicity of parts that are illustrated in necessarily somewhat crowded fashion, the individual parts have not been numbered in FIGS. 8, 9 and 10, but it will be understood that they correspond identically to those parts described and provided with reference numerals in FIG. 7.

FIGS. 8-13 clarify the overall operation of the apparatus 10. In FIG. 8, the apparatus is shown in the "pick up" position in which the syringe 12 has been previously filled with fluid, the plate 26 has been lowered, and suction applied through the cup 30 to engage an egg 21 maintained in the illustrated portion of an incubation tray broadly designated at 45.

FIG. 9 illustrates the next step in the process in which plate 26 has been raised while the suction is still being applied so that cups 30 in turn raise the eggs 21 out of the incubation tray that was illustrated in FIG. 8. FIG. 9 also illustrates that as plate 26 has been raised, plate 24 has been lowered (these may or may not take place concurrently depending upon the preferred operation) with the result that punch 16, and in particular its beveled tip, has punctured the shell of the egg 21.

Following puncture, FIG. 10 illustrates the downward movement of first plate 20 which in turn directs a downward movement of the injection needle 10 illustrated in FIG. 10 as penetrating slightly into the amniotic fluid of the egg 21. FIG. 10 also shows a slight downward movement of plate 22 by an amount which is calibrated to deliver the amount of fluid, typically a rather small volume, e.g. several microliters or less, that may desirably be injected.

Although not specifically illustrated, the operation of the apparatus continues in reciprocating fashion until the eggs 21 ar released.

Figure 11:
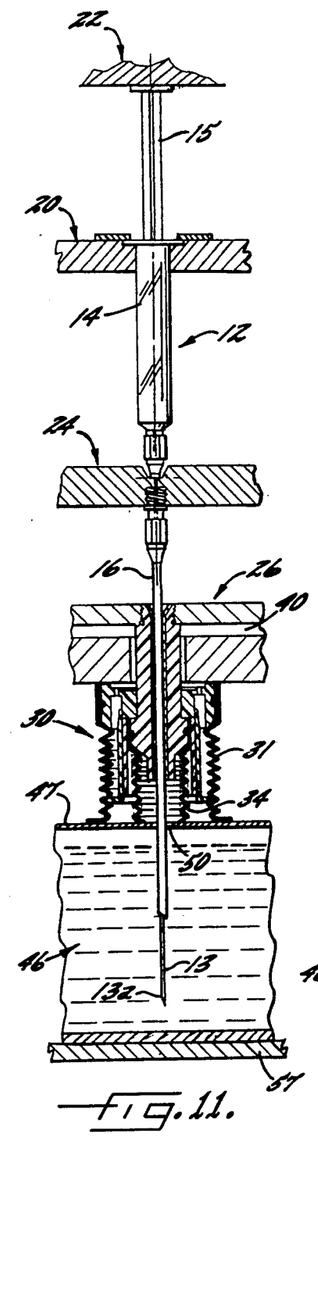
FIGS. 11 and 12 are also enlarged crosssectional views of a portion of the invention and particularly showing the cleaning cycles.
Figure 12:
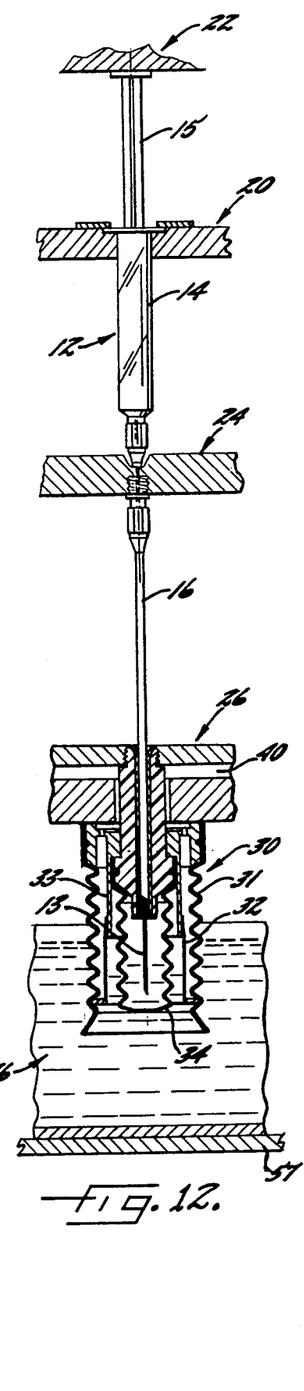
Figure 13:
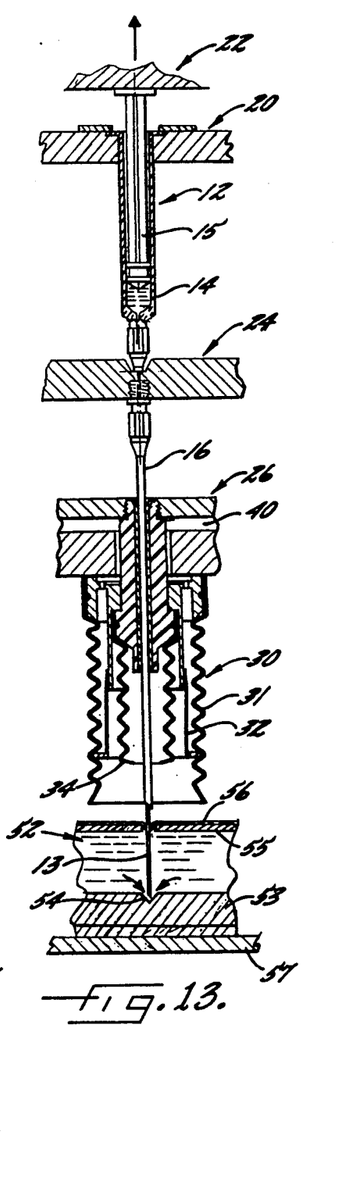
FIG. 13 is an enlarged cross-sectional view showing the filling cycle of the apparatus of the present invention.

FIGS. 11, 12 and 13 show various aspects of the cleaning and filling cycle of the apparatus 10. I n FIG. 11, the punch 16 and needle 13 have been lowered by the corresponding movements of plates 24 and 26 into a cleaning area which in the illustrated embodiment is a liquid bath 46 and which in preferred embodiments is an ultrasonic cleaning bath. As illustrated in FIG. 11, the bath 46 is kept as free as possible from contaminants by a cover plate 47 that includes a small opening 50 through which the punch 16 and needle 13 can extend while preventing to the extent possible entry of possible contaminants to the extent possible.

FIG. 12 illustrates a "deep clean" cycle which is performed somewhat less regularly than the cleaning cycle illustrated in FIG. 11. For example, the cleaning cycle of FIG. 11 may be repeated after each time the syringe dispenses fluid, while the cleaning cycle shown in FIG. 12 will typically take place less frequently. FIG. 12 illustrates that a larger portion of the cup 30 is introduced into the cleaning bath, which can be the same cleaning bath 46 described earlier including any ultrasonic applications. As illustrated in FIG. 12, both the outer and inner bellows 31 and 34 as well as the needle 10 can be cleaned in this fashion.

FIG. 13 shows the filling cycle in which the second plate 22 has been lowered relative to the first plate 20 so that the plunger 15 is positioned deep Within the barrel 14 of the syringe 12, plates 24 and 26 are also moved to a position in which the punch 16 extends downwardly through almost the entire extent of the cup 30 and so that the needle 13 specifically enters a reservoir, broadly designated at 52 in which the fluid to be injected into the eggs is kept. In FIG. 13, the reservoir is shown as having a floor 53 with recessed portions 54 which help ensure that the needle 13 is in contact with fluid rather than air as often as possible. The reservoir 52 is also illustrated as having a cover plate 55 and a flexible sealing web 56 that the needle punctures just prior to filling. The web 56, which can be formed of an appropriate laboratory-type paper or other suitable web material prevents the fluid in the reservoir from becoming contaminated as much as possible. In other embodiments which are not illustrated, the reservoir can be replaced with individual vials of fluid held in an appropriate rack so that a vial is aligned with each needle. The various ways of providing a supply of fluid underneath the needles are thus equivalent to that shown in FIG. 13.

For purposes of clarity, FIG. 13 shows the cup 30 suspended above the reservoir during the filling step. In a preferred embodiment, however, cup 30 is collapsed against cover plate 55 and sealing web 56 during the filling step.

Figure 2:
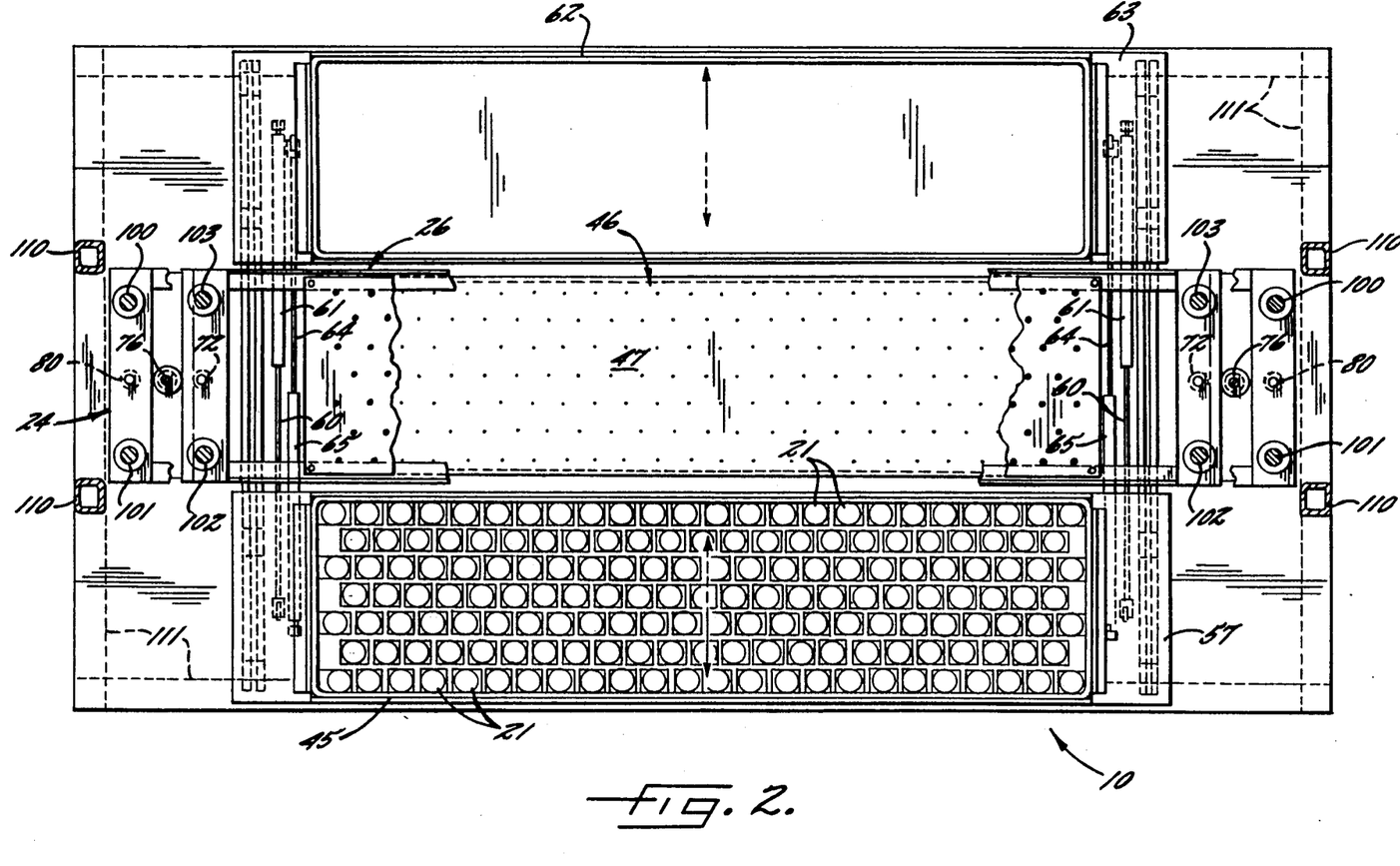
FIG. 2 is a plan view taken along lines 2—2 of FIG. 1.
Figure 3:
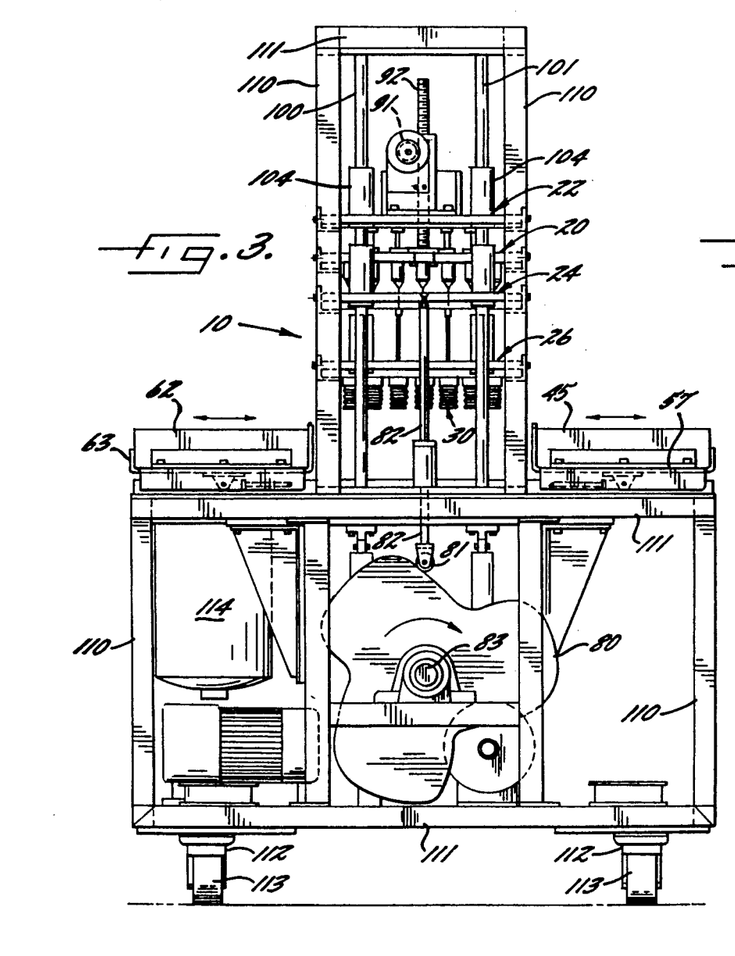
FIG. 3 is a side elevational view of the apparatus shown in FIG. 1.
Figure 4:
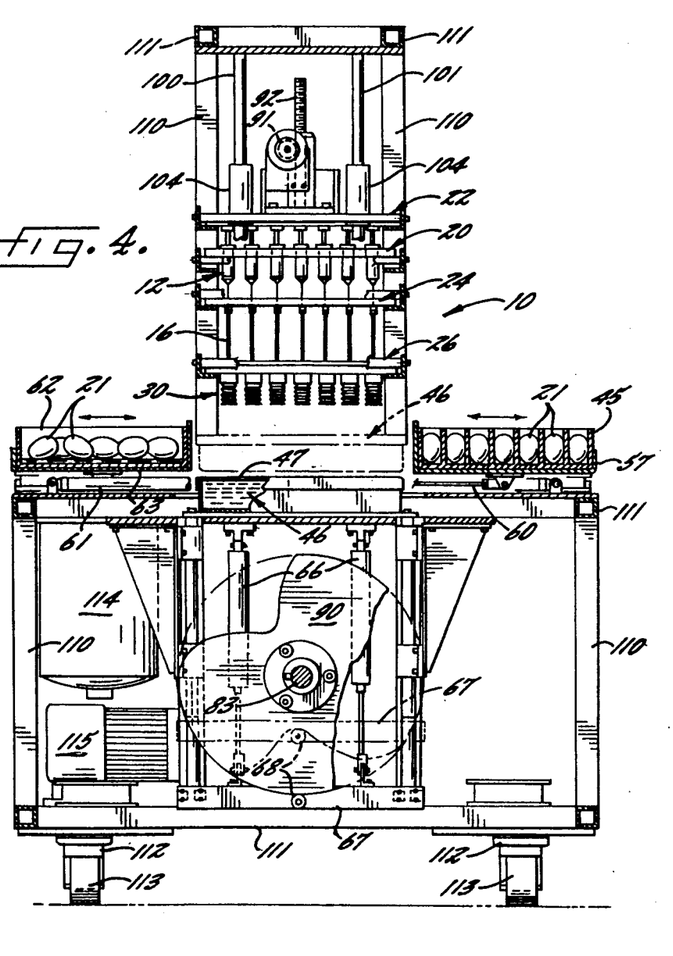
FIG. 4 is a partial elevational and partial cross-sectional view taken along lines 4—4 of FIG. 1.

FIGS. 2, 3 and 4 illustrate the means for aligning the injection needles 13 with the eggs 21 so that each needle 13, each surrounding punch 16, and each surrounding suction cup 30 is aligned with one respective egg 21. FIGS. 2 and 4 show that the eggs are initially maintained in an incubation tray 45 which holds the eggs upright in particular positions in a desired pattern. The incubation tray 45 rests on a horizontally movable platform 57 that is moveable between respective loading and injection positions. The injection position is disposed substantially directly below the injection needles 13 so that the incubation tray 45 aligns each respective egg 21 with one respective needle 13. The moveable platform 57 comprises at least one horizontally disposed and horizontally extendable reciprocating shaft 60 connected to the platform 57 and means shown as the cylinder 61 for horizontally reciprocating the shaft 60 to thereby provide horizontal movement to the platform 57 and to the incubation tray 45 thereon.

The apparatus 10 further comprises means for transferring the eggs following injection into a hatching tray illustrated at 62. The means for transferring the egg into the hatching tray comprises another platform 63 that is horizontally moveable between a respective first position underneath the injection needles 10 and a second position laterally offset from the first position in a direction towards one side of the apparatus 10. Eggs that are released from the suction cups 30 can be received in a hatching tray 62 upon the platform 63 in the first position and the hatching tray 62 carrying the released eggs can be moved to the second position for removal from the apparatus 10 and subsequent hatching of the eggs. It will be understood by those familiar with the incubation and hatching of eggs that although the eggs can be incubated while maintained in a regular upright position in the incubation tray 40 as illustrated, the eggs must be released and permitted to orient themselves in a more horizontal position in order to provide newly hatched chicks with unencumbered mobility As in the case of the movement of the platform 57, the movement of platform 63 is likewise accomplished by a reciprocating shaft 64 driven by a cylinder 65 (FIG. 2). As illustrated, a pair of shafts 64 and a pair of cylinders 65 can be used to move the platform 63, and a corresponding pair of shafts 60 and cylinders 61 can be used to move the platform 57.

FIG. 4 in particular illustrates that the cleaning bath 46 is positioned directly below the injection position of the apparatus 10 so the needles 13 can be aligned with and inserted into the bath 46 when the horizontally moveable platform 57 is in the loading position. In a preferred embodiment, the bath 46 is vertically moveable from a position defined by its alignment with the needles 13 to a lower position therebeneath for being more conveniently cleaned or filled with fluids in the lower position This is perhaps best illustrated in FIG. 4 in which the bath 46 is shown as mounted on a pair of cylinders 66 which can raise and lower the bath 46 as needed or desired. The cylinders 66 urge a cross member 67 upward, and the cross member 67 carries the respective cam follower 68. Thus, as cam 90 rotates follower 68 and cross member 67 can move between the respective illustrated positions and raise and lower the bath 46.

All of the various cylinders and their connection to the parts they move are generally conventional in nature and will not be described in further detail herein other than to point out that the appropriate arrangements can be made without undue experimentation in manufacturing or operating the device.

Additionally, with regard to the filling steps described earlier, the reservoir 52 is preferably placed on the platforms 57 and moved into position in a manner identical to that in which either of the tray 45 is positioned during the injection and transfer cycle.

FIGS. 1, and 3-6 also illustrate in further detail the means for moving each of the first, second, third and fourth plates in vertical relationship with one another so that the suction cups 30 can engage a respective plurality of eggs 21, the punches 16 can form an opening in each respective egg, and each of the injection needles 13 can extend into an egg and deliver fluid there into. In the preferred embodiment, the plate moving means for the first, third and fourth plates 20, 24, and 26 each respectively comprises a shaft associated with each plate so that the plate and shaft are moveable together, a rotating cam, and a follower on each shaft for being positioned upon and following the edge of the cam. The rotation of the cam defines a path for, and imparts movement to, the follower, and through the follower to the shaft and the plate to thereby raise and lower the plate.

FIG. 1 illustrates three pairs of rotating cams. An innermost pair for which each cam is designated at 70 operates the fourth plate 26 and the suction cups 30 it carries. Each cam 70 is followed by a follower assembly 71 which in turn is connected to a shaft 72 that raises and lowers plate 26 A second pair of cams designated at 74 operates through follower assembly 75 and shaft 76 to raise and lower the first plate 20 and the needles 13. A third and outermost pair of cams designated at 80 operate through follower assembly 81 and shaft 82 to correspondingly move the third plate 24 and the punches 16.

The cams are all fixed to respective axles 83 driven in turn by an appropriate motor 84 through transmission mechanisms 85 and 86. The axle 83 can also be used to drive yet another pair of cams 90 which operate in conjunction with the cylinders 66 to raise and lower the reservoir 52 as described earlier.

The second plate 22 which controls the plungers 15 and thereby the amount of fluid delivered, is moved in somewhat different fashion. Because of the very small volumes of fluid which are typically delivered to each egg 20, often several of microliters or less, the cam and shaft mechanism used to move the other plates may not be precise enough for controlling the plungers in a desired fashion. Therefore, in a preferred embodiment, the second plate 22 is controlled by either a stepping motor (not shown) which can produce small increments of movement, or by the arrangement shown in FIG. 1 in which a motor 87 drives a pinion gear 91 on a threaded shaft 92 (illustrated as a pair of threaded shafts on opposite sides of the apparatus 10, and referred to as a "jack screw") to precisely control the movement of the plungers and thereby the volume of fluid delivered.

FIG. 5 illustrates some of these features in further detail and shows that the motor 87 is connected to the follower 91 by a driving pulley 93 and a driven pulley 94 connected by a belt 95. The driven pulley 94 in turn drives shaft 96 which in turn drives the opposite follower 91 on the opposite shaft 92

FIGS. 1, 5 and 6, among others, also illustrate that the movement of the plates is stabilized by four vertical shafts 100, 101, 102 and 103 respectively on each end of the apparatus 10 and along which the respective plates move on bearings 104. The shafts and bearings stabilize the vertical movement of the respective plates as they are driven by one of the cams, followers and shafts as illustrated in partial fashion in FIG. 6. In particular, FIG. 6 illustrates the third plate 24 including a platen 105 in which the punches 16 may be mounted.

A number of other features of the apparatus 10 will now be described. The entire apparatus is assembled on a framework comprised of a plurality of vertical members 110 and horizontal members 111. The entire apparatus is mounted on casters 112 and wheels 113 so that it can be moved from place to place if desired.

FIG. 3 illustrates a holding tank 114 for fluid, which may be the fluid used in the reservoir 52 as well as an additional motor assembly 115 that can be used in conjunction with those already described to drive the various portions of the apparatus 10. The illustration of FIG. 3 also shows one of the cams 80, follower assembly 81 and shaft 82 complimenting the illustration of these elements shown in FIG. 1. FIG. 1 also shows that an ultrasonic generator 117 can be included as part of the cleaning features if so desired.

Because of the advantages provided by the apparatus 10, the invention also includes the method of automatically injecting eggs with fluids which eliminates manual handling of eggs and which eliminates the pumping of fluids through a conventional fluid handling systems. The invention thereby increases the accuracy and precision of volume delivery while eliminating much of the possibility of contamination of the fluid and the system. The method comprises mechanically aligning the delivery tip of a syringe with a fluid containing reservoir, inserting the delivery tip of the syringe into the fluid containing reservoir, drawing fluid from the reservoir through the delivery tip and into the syringe, mechanically aligning an egg with the syringe, forming a small opening in a selected portion of the egg aligned with the delivery tip of the syringe, inserting the delivery tip of the syringe through the aligned opening in the egg, and dispensing the fluid from syringe into the egg. As already described, the step of forming an aligned opening in the egg comprises punching an opening in the egg as well as removing the syringe from the egg following the step of dispensing the fluid from the syringe into the egg.

Alternatively, the invention can be considered to comprise the steps of aspirating a predetermined amount of fluid into each of a plurality of syringes aligned with respect to one another by aspirating the fluid through the delivery tip of each syringe, aligning a plurality of eggs under the plurality of syringes so that one syringe is aligned with each egg, lifting the eggs with respect to the syringes while maintaining their alignment with respect to the syringes, punching a hole in each egg using a plurality of punches, each one of which is aligned with one syringe and one egg, moving the delivery tip of each syringe downwardly into each respective egg, and delivering a predetermined amount of fluid from the delivery tip of each syringe into each egg. In this context, the step of lifting the eggs comprises lifting the eggs using suction and the step of aligning the eggs with the syringes comprises aligning an incubation tray carrying a plurality of eggs with the syringes so that each of the eggs in the incubation tray is aligned with one syringe. As described earlier, the step of aspirating fluid into the syringes comprises raising a respective plunger within each of the barrels of each syringe and the step of delivery fluid from the syringes comprises lowering the respective plunger within each of the barrels. In a further refinement of the invention, the invention includes moving a setting tray containing a plurality of eggs under the plurality of syringes s that one syringe is aligned with each egg, removing the setting tray from beneath the lifted eggs and replacing the setting tray with a hatching tray, and then releasing the eggs into the hatching tray following injection.

As described earlier, in a preferred embodiment of the invention and use of the apparatus, the method further comprises lowering the delivery tips of the syringes and the punches into a cleaning bath following the step o releasing the eggs into the hatching tray.

In the drawings and specification, there have been disclosed typical preferred embodiments of the invention and, although specific terms have been employed, they have been used in a generic and descriptive sense only and not for purposes of limitation, the scope of the invention being set forth in the following claims.

That which I claim is:

1. An apparatus for automatically injecting eggs with a desired fluid such as a medical vaccine or a therapeutic preparation and which eliminates the pumping of fluids through conventional fluid handling systems and thereby increases the accuracy and precision of a volume delivery while eliminating much of the possibility of contamination of the fluid and the system, the apparatus comprising:

a syringe having a delivery tip comprising an injection needle and a portion for containing a predetermined quantity of fluid;

means operatively associated with said syringe for intaking and delivering controllable amounts of fluids through said delivery tip of said syringe;

means for positioning a fluid reservoir in alignment with said delivery tip of said syringe so that fluid from said reservoir may be intaken through said delivery tip and into said fluid containing portion of said syringe;

means for supporting an egg in alignment with said syringe;

a tubular punch surrounding portions of said injection needle for puncturing the upwardly facing shell portion of an egg aligned with said syringe and for forming a small opening in the shell of a supported egg;

means for moving said syringe and a supported egg in relation to one another so that the delivery tip of said syringe extends through the opening in the egg formed by said opening forming means so that said intake and delivery means can deliver a fluid through said delivery tip, through the opening and into the egg to be treated by the fluid.

2. An apparatus according to claim 1 further comprising means for aligning said syringe and the small opening in the egg in a predetermined position with respect to one another.

3. An apparatus according to claim 2 wherein said egg supporting means comprises;

a flexible cup surrounding portions of said syringe for being received in seated sealing relation against upwardly facing shell portions of the egg; and means for providing suction to said cups so that the suction seats the upwardly facing shell portions of an egg against said cup in a predetermined aligned position with respect to said syringe.

4. An apparatus according to claim 1 wherein said tubular punch has a beveled tip for facilitating formation of the opening in the egg.

5. An apparatus for automatically injecting eggs with a desired fluid such as a medical vaccine or a therapeutic preparation and which eliminates the pumping of fluids through conventional fluid handling systems and thereby increases the accuracy and precision of a volume delivery while eliminating much of the possibility of contamination of the fluid and the system, the apparatus comprising:

- a first horizontally disposed and vertically movable plate having a plurality of downwardly vertically disposed injection syringes fixed thereto so that the movement of said syringes follows the vertical movement of said first plate, each syringe comprising an injection needle, a fluid holding barrel, and a plunger for being moved within said barrel for drawing fluids into and forcing fluids out of said barrel through said injection needle;
- a second horizontally disposed and vertically moveable plate positioned above said first plate and connected to the plungers so that the movement of said plungers follows the movement of said second plate to thereby draw fluid into or force fluid out of said barrel through said injection needle as said second plate moves in a vertical fashion;
- a third horizontally disposed and vertically moveable plate positioned below said first plate and carrying a plurality of punches, each of which respectively surrounds one of said injection needles depending from said first plate for forming a small opening in the shell of an egg so that the vertical movement of said punches follows the vertical movement of said third plate;
- a fourth horizontally disposed and vertically moveable plate positioned below said third plate and carrying a plurality of flexible suction cups, with each of said suction cups respectively surrounding one of said punches which respectively surrounds one of said injection needles, and for being received in seated sealing relation against upwardly facing shell portions of an egg;
- a reservoir for containing fluid therein positioned underneath said injection needles;
- means for aligning said injection needles with said fluid-containing reservoir so that said needles can draw fluid directly from said reservoir;
- means for aligning a plurality of eggs with said injection needles so that each needle, surrounding punch, and surrounding suction cup is aligned with one respective egg; and
- means for moving each of said first, second, third, and fourth plates in vertical relationship with one another so that said injection needles can draw fluid directly from said reservoir, said suction cups can engage a respective plurality of eggs, said punches can form an opening in each respective egg, and each of said injection needles can extend into an egg and deliver fluid thereinto.

6. An apparatus according to claim 5 wherein said egg and needle aligning means comprise a horizontally movable platform and in incubation tray upon said platform, said platform being movable between respective loading and injection positions, with said loading position being laterally offset from said injection needles and with said injection position being disposed substantially directly below said injection needles so that said incubation tray aligns each respective egg therein with one respective needle.

7. An apparatus according to claim 6 further comprising a cleaning path wherein said fluid containing reservoir is positioned directly below said injection position so that said needles can be aligned with and inserted into said cleaning path when said horizontally movable platform is in said loading position.

8. An apparatus according to claim 7 wherein said cleaning bath is vertically moveable from a position defined by its alignment with said needles to a lower position therebeneath for being move conveniently cleaned or filled with fluid in the lower position.

9. An apparatus according to claim 6 wherein said movable platform further comprises:
- at least one horizontally disposed and horizontally extensible reciprocating shaft connected to said platform; and
- means for horizontally reciprocating said shaft to thereby provide horizontal movement to said platform and to said incubation tray thereon.

10. An apparatus according to claim 5 wherein said plate moving means comprises:
- a shaft associated with each said plate so that said plate and said shaft are moveable together;
- a rotating cam; and
- a follower on said shaft for being positioned upon and following the edge of said rotating cam so that rotation of said cam defines a path for said follower and imparts movement to said follower, and through said follower to said shaft and said plate that raises and lowers said plate.

11. An apparatus according to claim 5 further comprising means for transferring eggs following injection into a hatching tray.

12. An apparatus according to claim 11 wherein said means for transferring the eggs into a hatching tray comprises a platform horizontally moveable between a respective first position underneath said syringes and a second position laterally offset from said first position in a direction towards one side of said apparatus so that eggs released from said suction cups may be received in a hatching tray upon said platform in said first position and a hatching tray carrying released eggs can be moved to said second position for removal from said apparatus and subsequent hatching of the eggs.

13. An apparatus according to claim 5 wherein each said flexible suction cup further comprises:
- means for controlling the collapse of said cup when suction is applied thereto; and
- means for preventing suction from being applied through the punch-formed opening in an egg while the egg is held in seated sealing relation with said suction cup when suction is applied through said cup.

14. A suction cup apparatus for engaging an egg in seated sealing relation therewith and comprising:
- a generally cylindrical and collapsible outer bellows through which suction can be applied to the shell of an egg when said outer bellows is in contact with the egg; and
- a generally cylindrical and collapsible inner bellows positioned coaxially within said outer bellows and forming an annular channel between said inner bellows and said outer bellows, and wherein said inner bellows limits the path through which suction can be applied to said annular channel, and thereby prevents suction that is applied through said outer bellows from reaching or affecting the shell portions of an egg inside said inner bellows.

15. A suction cup according to claim 14 further comprising an inner relatively rigid sliding cylinder positioned coaxially with said inner and outer bellows for controlling the collapse of said inner and outer bellows when suction is through said cup.

16. A suction cup according to claim 15 wherein said outer bellows is connected to said cylinder s that the movement of said bellows during collapse slides said cylinder along the direction of collapse.

17. A suction cup according to claim 16 and further comprising:
   an injection needle positioned inside of and coaxially with said inner bellows;
   a tubular punch surrounding portions of said injection needle for puncturing the upwardly facing shell portion of an egg engaged by said suction cup and delivering a fluid to the egg from said injection needle; and
   means for drawing a suction in said annular channel between said inner bellows and said outer bellows.

18. A method of automatically injecting eggs with fluids which eliminates manual handling of eggs and which eliminates the pumping of the fluids through conventional fluid handling systems and thereby increases the accuracy and precision of volume delivery while eliminating much of the possibility of contamination of the fluid and the system, the method comprising:
   (a) aligning the delivery tip of a syringe with a fluid containing reservoir;
   (b) inserting the delivery tip of the syringe into the fluid-containing reservoir;
   (c) drawing fluid from the reservoir through the delivery tip and into the syringe;
   (d) aligning an egg with the syringe;
   (e) forming a small opening in a selected portion of the egg aligned with the delivery tip of the syringe;
   (f) thereafter inserting the delivery tip of the syringe through the aligned opening in the egg; and then
   (g) delivering the fluid from the syringe into the egg.

19. A method according to claim 18 further comprising the steps of:
   removing the syringe from the egg following the step of delivering the fluid from the syringe into the egg; and then
   cleaning the delivery tip of the syringe; and then repeating steps (d) through (g).

20. A method according to claim 18 wherein the step of forming an aligned opening in the egg comprises punching an opening in the egg.

21. A method of automatically injecting eggs with fluids which eliminates manual handling of egg and which eliminates the pumping of the fluids through conventional fluid handling systems and thereby increases the accuracy and precision of volume delivery while eliminating much of the possibility of contamination of the fluid and the system, the method comprising:
   (a) aspirating a predetermined amount of fluid into each of a plurality of syringes aligned with respect to one another by aspirating the fluid through the delivery tip of each syringe;
   (b) aligning a plurality of eggs under the plurality of syringes so that one syringe is aligned with each egg;
   (c) lifting the eggs while maintaining their alignment with respect to the syringes;
   (d) punching an opening in each lifted egg using a plurality of punches, each one of which is aligned with one syringe and one egg;
   (e) moving the delivery tip of each syringe downwardly into each respective egg through the punched opening; and
   (f) delivering a predetermined amount of fluid from the delivery tip of each syringe into each egg.

22. A method according to claim 21 further comprising the steps of:
   removing the syringes from the eggs following the step of delivering the fluid from the syringe into the egg; and then
   releasing the lifted eggs; and then
   cleaning the delivery tip of each syringe; and then repeating steps (b) through (f).

23. A method according to claim 21 wherein the step of lifting the eggs comprises lifting the eggs using suction.

24. A method according to claim 21 wherein the step of aligning the eggs with the syringes comprises aligning an incubation tray carrying a plurality of eggs with the syringes so that each of the eggs in the incubation tray is aligned with one syringe.

25. A method according to claim 21 wherein the syringes comprise fluid containing barrels with plungers therein and wherein the step of aspirating fluid into the syringes comprises raising the respective plunger within each of the barrels and the step of delivering fluid from the syringes comprises lowering the respective plunger within each of the barrels.

26. A method of automatically injecting eggs with fluids which eliminates manual handling of eggs and which eliminates the pumping of the fluids through conventional fluid handling systems and thereby increases the accuracy and precision of volume delivery while eliminating much of the possibility of contamination of the fluid and the system, the method comprising:
   (a) aspirating a predetermined amount of fluid into each of a plurality of syringes aligned with respect to one another by aspirating the fluid through the delivery tip of each syringe;
   (b) moving a setting tray containing a plurality of eggs under the plurality of syringes so that one syringe is aligned with each egg;
   (c) lifting the eggs out of the setting tray while maintaining their alignment with respect to the syringes;
   (d) punching an opening in each egg using a plurality of punches, each one of which is aligned with one syringe and one egg;
   (e) moving the delivery tip of each syringe downwardly into each respective egg through the punched opening;
   (f) delivering a predetermined amount of fluid from the delivery tip of each syringe into each egg;
   (g) removing the setting tray from beneath the lifted eggs and replacing it with a hatching tray; and
   (h) releasing the eggs into the hatching tray.

27. A method according to claim 26 further comprising removing the hatching tray and the released eggs contained therein from beneath the syringes.

28. A method according to claim 26 further comprising lowering the delivery tips of the syringes and the punches into a cleaning bath following the step of releasing the eggs into the hatching tray.

29. A method according to claim 28 further comprising removing the delivery tips of the syringes and the punches from the cleaning bath and then repeating steps (a) through (h).

* * * * *

UNITED STATES PATENT AND TRADEMARK OFFICE
CERTIFICATE OF CORRECTION

PATENT NO. : 5,056,464
DATED : October 15, 1991
INVENTOR(S) : Robert H. Lewis

It is certified that error appears in the above-identified patent and that said Letters Patent is hereby corrected as shown below:

At line 7, "such" should be -- much --.

At column 3, line 14, "crosssectional" should be -- cross-sectional --.

At column 4, line 2, "10" should be -- 13 --.

At column 4, line 8, "10" should be -- 13 --.

At column 4, line 54, "Cylinder" should be -- cylinder --.

At column 6, line 7, "ar" should be -- are --.

At column 6, line 9, "I n" should be -- In --.

At column 6, line 31, "10" should be -- 13 --.

At column 6, line 34, "Within" should be -- within --.

At column 6, line 35, "12, plates" should be -- 12. Plates --

At column 7, line 17, "10" should be -- 13 --.

UNITED STATES PATENT AND TRADEMARK OFFICE
CERTIFICATE OF CORRECTION

PATENT NO. : 5,056,464
DATED : October 15, 1991
INVENTOR(S) : Robert H. Lewis

It is certified that error appears in the above-identified patent and that said Letters Patent is hereby corrected as shown below:

At column 7, line 28, "40" should be -- 45 --.

At column 8, line 41, "20" should be -- 21 --.

At column 9, line 1, "Will" should be -- will --.

At column 9, line 67, "s" should be -- so --.

At column 10, line 8, "o" should be -- of --.

IN THE CLAIMS:

At column 11, line 66, "path" should be -- bath --.

At column 12, line 1, "path" should be -- bath --.

At column 12, line 6, "move" should be -- more --.

At column 13, line 4, "s" should be -- so --.

Signed and Sealed this

Twentieth Day of July, 1993

Attest:

MICHAEL K. KIRK

Attesting Officer

Acting Commissioner of Patents and Trademarks